(12) United States Patent
Ago et al.

(10) Patent No.: US 11,234,777 B2
(45) Date of Patent: Feb. 1, 2022

(54) ADAPTOR AND ROBOTIC SURGICAL SYSTEM

(71) Applicants: MEDICAROID CORPORATION, Kobe (JP); KAWASAKI JUKOGYO KABUSHIKI KAISHA, Kobe (JP)

(72) Inventors: Kenji Ago, Kobe (JP); Koji Muneto, Kobe (JP)

(73) Assignees: MEDICAROID CORPORATION, Kobe (JP); KAWASAKI JUKOGYO KABUSHIKI KAISHA, Kobe (JP)

( * ) Notice: Subject to any disclaimer, the term of this patent is extended or adjusted under 35 U.S.C. 154(b) by 180 days.

(21) Appl. No.: 16/823,332

(22) Filed: Mar. 19, 2020

(65) Prior Publication Data
US 2020/0305990 A1 Oct. 1, 2020

(30) Foreign Application Priority Data
Mar. 28, 2019 (JP) .............................. JP2019-063490

(51) Int. Cl.
| | |
|---|---|
| *A61B 34/30* | (2016.01) |
| *A61B 46/10* | (2016.01) |
| *A61B 90/50* | (2016.01) |
| A61B 34/37 | (2016.01) |
| A61B 34/00 | (2016.01) |
| A61B 17/00 | (2006.01) |

(52) U.S. Cl.
CPC .............. *A61B 34/30* (2016.02); *A61B 46/10* (2016.02); *A61B 90/50* (2016.02); *A61B 34/37* (2016.02); *A61B 34/71* (2016.02); *A61B 2017/00221* (2013.01); *A61B 2017/00486* (2013.01)

(58) Field of Classification Search
CPC combination set(s) only.
See application file for complete search history.

(56) References Cited

U.S. PATENT DOCUMENTS

| 7,666,191 B2 | 2/2010 | Orban, III et al. |
|---|---|---|
| 2006/0161138 A1 | 7/2006 | Orban, III et al. |
| 2010/0170519 A1 | 7/2010 | Romo et al. |
| 2010/0174293 A1 | 7/2010 | Orban, III et al. |
| 2012/0247489 A1 | 10/2012 | Orban, III et al. |

FOREIGN PATENT DOCUMENTS

| JP | 5403864 B2 | 1/2014 |
|---|---|---|
| WO | 2011/037394 A2 | 3/2011 |
| WO | 2017/205333 A1 | 11/2017 |

*Primary Examiner* — Scott Luan
(74) *Attorney, Agent, or Firm* — Metrolex IP Law Group, PLLC

(57) ABSTRACT

An adaptor according to one or more embodiments may include a drive transmission member to transmit a driving force from a driving member of a drive part to a driven member of a surgical instrument. The drive transmission member may include: a first member to be fitted to the driven member of the surgical instrument; and a second member relatively movable with respect to the first member in directions toward the surgical instrument and toward the drive part and to be fitted to the driving member. The second member may include a movement restriction part that comes in contact with the driven member to restrict a movement of the second member toward the surgical instrument in a state where the driving member of the drive part is fitted to the second member and the driven member of the surgical instrument is fitted to the first member.

20 Claims, 9 Drawing Sheets

FIG. 6A
FIG. 6B
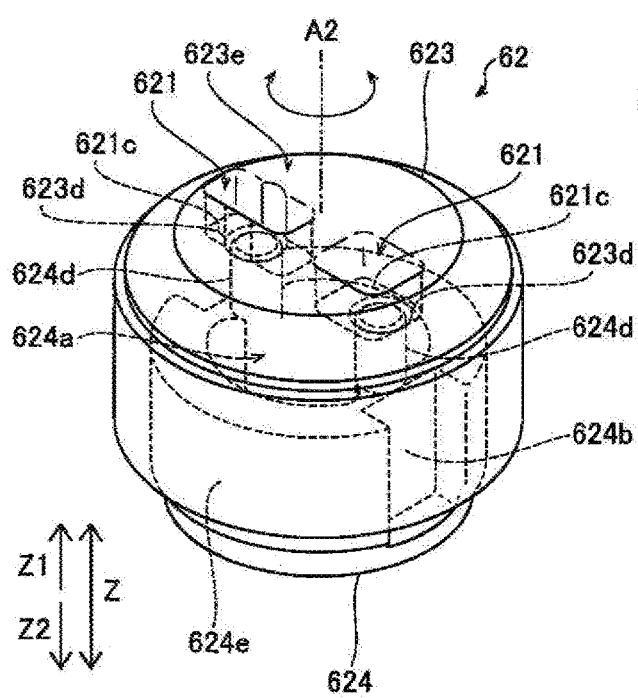
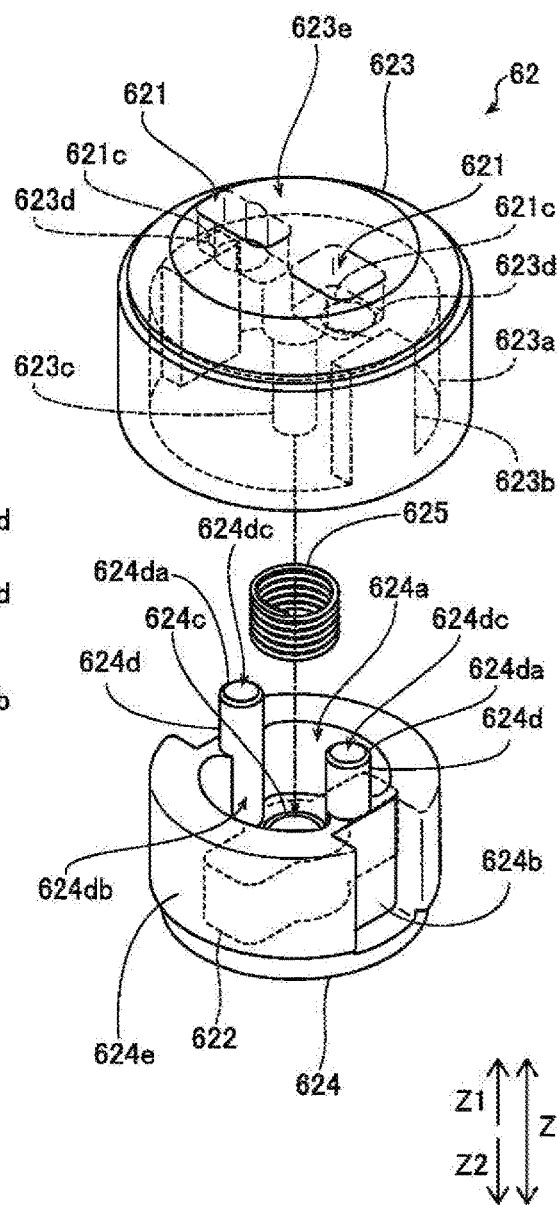

ADAPTOR IS MOUNTED BUT NOT FITTED

ADAPTOR IS MOUNTED AND FITTED

SURGICAL INSTRUMENT IS MOUNTED BUT NOT FITTED

SURGICAL INSTRUMENT IS MOUNTED AND FITTED (MODIFICATION)

SURGICAL INSTRUMENT IS MOUNTED AND FITTED

ADAPTOR AND ROBOTIC SURGICAL SYSTEM

CROSS-REFERENCE TO RELATED APPLICATIONS

This application claims priority to Japanese Patent Application No. 2019-063490 filed on Mar. 28, 2019, the entire contents of which are incorporated herein by reference.

BACKGROUND

The disclosure may relate to an adaptor, and more specifically relate to an adaptor provided between a drive part and a surgical instrument and a robotic surgical system including the drive part, the surgical instrument, and the adaptor.

Robotic surgical systems for assisting surgery are known. Such robotic surgical systems generally include a patient-side apparatus with robot arms and a remote control apparatus for remote control of the patient-side apparatus. To the robot arms of the patient-side apparatus, an endoscope to capture an image within a body of a patient and surgical instruments including an end effector to perform surgery for the patient are attached. A doctor performs endoscopic surgery for the patient by operating the remote control apparatus to operate the patient-side apparatus while checking endoscopic images in the patient's body. Using such a robotic surgical system minimizes the incision in the patient's skin in the surgery, enabling minimally invasive surgery with the burden on the patient reduced.

Japanese Patent No. 5403864 discloses a robotic surgical system including an adaptor receiving portion as a driving part; a surgical instrument attached to the adaptor receiving portion; and an instrument sterile adaptor provided between the adaptor receiving portion and the surgical instrument. The instrument sterile adaptor includes a disk to transmit a driving force from the adaptor receiving portion to the surgical instrument. The disk includes a hole in which a pin of the surgical instrument is fitted and a hole in which a pin of a spring load input of the adaptor receiving portion is fitted.

SUMMARY

However, the robotic surgical system disclosed in Japanese Patent No. 5403864, when the surgical instrument is mounted to the adaptor receiving portion, the spring load input is moved in directions toward the surgical instrument and toward the adaptor receiving portion (the driving part). Therefore, the spring load input may be worn during a long-term use. Further, since the adaptor receiving portion having the spring load input is provided at a robot arm, it may be difficult for a user to replace the spring load input.

An object of an aspect of the disclosure is to make it possible for a user to easily replace a component that moves in directions toward the surgical instrument and toward the drive part when the surgical instrument is mounted to the drive part.

In order to achieve the above object, inventors of the disclosure have conceived to provide a component that moves in directions toward a surgical instrument and toward a drive part when the surgical instrument is mounted to the drive part, at an adaptor, which is to be replaced by a user, but not at the drive part of an robot arm.

An aspect of the disclosure may be an adaptor to be provided between a drive part provided at a robot arm and including a driving member and a surgical instrument including a driven member. The adaptor includes a drive transmission member provided to be rotatable to transmit a driving force from the driving member of the drive part to the driven member of the surgical instrument. The drive transmission member includes: a first member to be fitted to the driven member of the surgical instrument; and a second member relatively movable with respect to the first member in directions toward the surgical instrument and toward the drive part, the second member being to be fitted to the driving member of the drive part. The second member includes a movement restriction part that comes in contact with the driven member of the surgical instrument to restrict a movement of the second member toward the surgical instrument in a state where the driving member of the drive part is fitted to the second member and the driven member of the surgical instrument is fitted to the first member.

Another aspect of the disclosure may be an adaptor to be provided between a drive part provided at a robot arm and including a driving member and a surgical instrument including a driven member. The adaptor includes a drive transmission member provided to be rotatable to transmit a driving force from the driving member of the drive part to the driven member of the surgical instrument. The drive transmission member includes: a first member to be fitted to the driven member of the surgical instrument; and a second member relatively movable with respect to the first member in directions toward the surgical instrument and toward the drive part, the second member being to be fitted to the driving member of the drive part. The second member includes a movement restriction part that is in contact with the driven member of the surgical instrument to restrict a movement of the second member toward the surgical instrument in a state where the driving member of the drive part is fitted to the second member and the driven member of the surgical instrument is fitted to the first member.

A still another aspect of the disclosure may be a robotic surgical system that includes: a drive part provided at a robot arm and including a driving member; a surgical instrument including a housing to be attached to the drive part and a driven member rotatably provided in the housing; and an adaptor to be provided between the drive part and the surgical instrument. The adaptor includes: a drive transmission member provided to be rotatable to transmit a driving force from the driving member of the drive part to the driven member of the surgical instrument. The drive transmission member includes: a first member to be fitted to the driven member of the surgical instrument; and a second member relatively movable with respect to the first member in directions toward the surgical instrument and toward the drive part, the second member being to be fitted to the driving member of the drive part. The second member includes a movement restriction part that comes in contact with the driven member of the surgical instrument to restrict a movement of the second member toward the surgical instrument in a state where the driving member of the drive part is fitted to the second member and the driven member of the surgical instrument is fitted to the first member.

BRIEF DESCRIPTION OF THE DRAWINGS

FIG. 6A is a diagram illustrating a perspective view of a drive transmission member of the adaptor according to an embodiment.

FIG. 6B is a diagram illustrating an exploded perspective view of the drive transmission member of the adaptor according to an embodiment.

DETAILED DESCRIPTION

Figure 1:
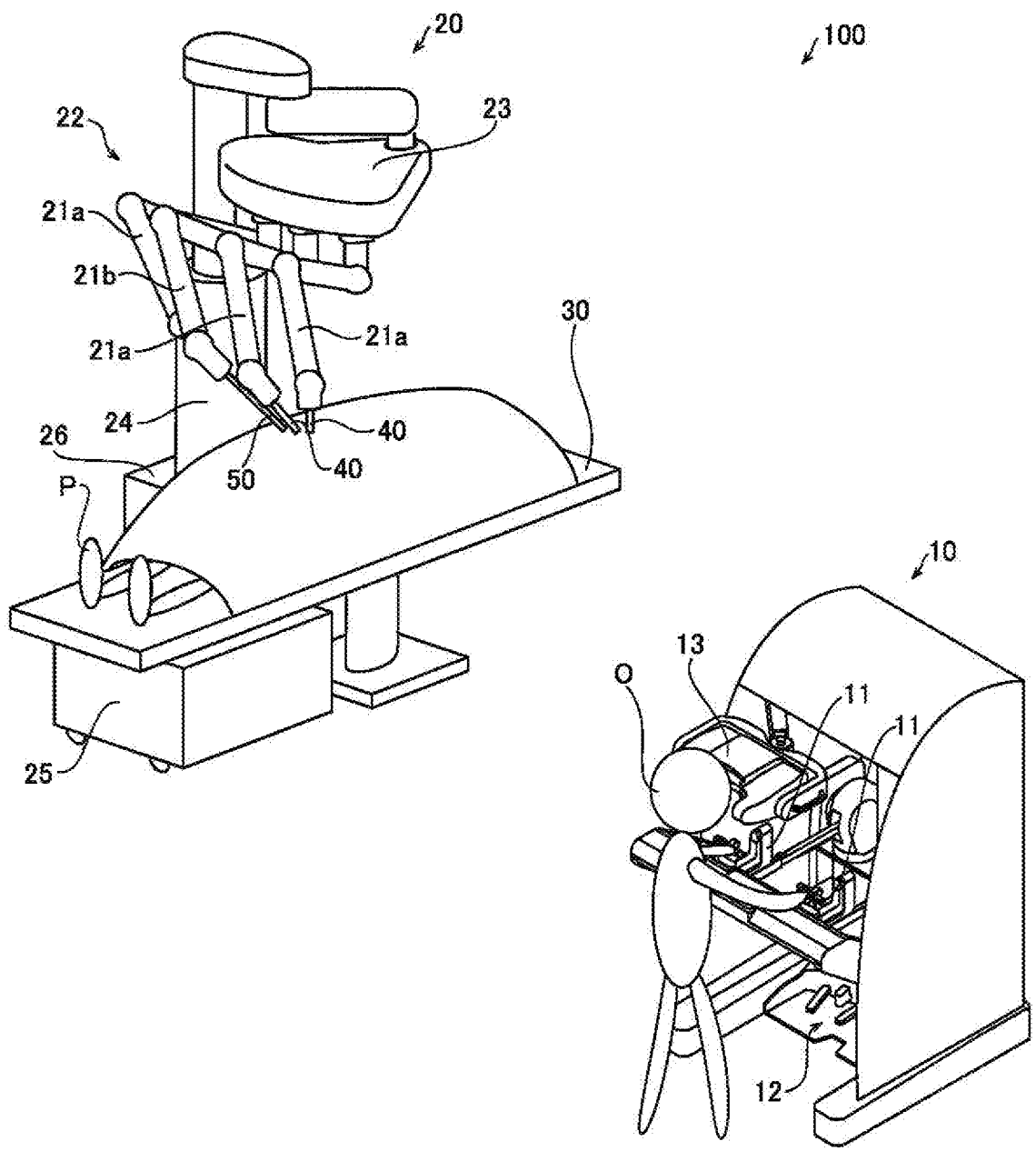
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

The configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 attached to robot arms 21a and an endoscope 50 attached to a robot arm 21b. This allows for minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21a and 21b. One robot arm 21b holds the endoscope 50 while the other robot arms 21a hold the surgical instruments 40. The robot arms 21a and 21b are commonly supported by a platform 23. Each of the plural robot arms 21a and 21b includes plural joints. Each joint includes a driver provided with a servo-motor and a position detector such as an encoder. The robot arms 21a and 21b are configured so that the medical equipment attached to each of the robot arms 21a and 21b is controlled by a driving signal given through the controller 26 and performs a desired movement.

The platform 23 is supported by a positioner 22 placed on a floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment is detachably attached to the distal ends of the robot arms 21a. Each surgical instrument 40 includes: a housing 43 (see FIG. 4), which is attached to the robot arm 21a; an elongated shaft 42 (see FIG. 4); and an end effector 41 (see FIG. 4), which is provided at the distal end portion of the shaft 42. The end effector 41 may be grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effector 41 of the surgical instrument 40 is then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures)

and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include setting of the position and posture of the distal end portion of the endoscope 50 and setting of the zoom magnification, for example.

Figure 2:
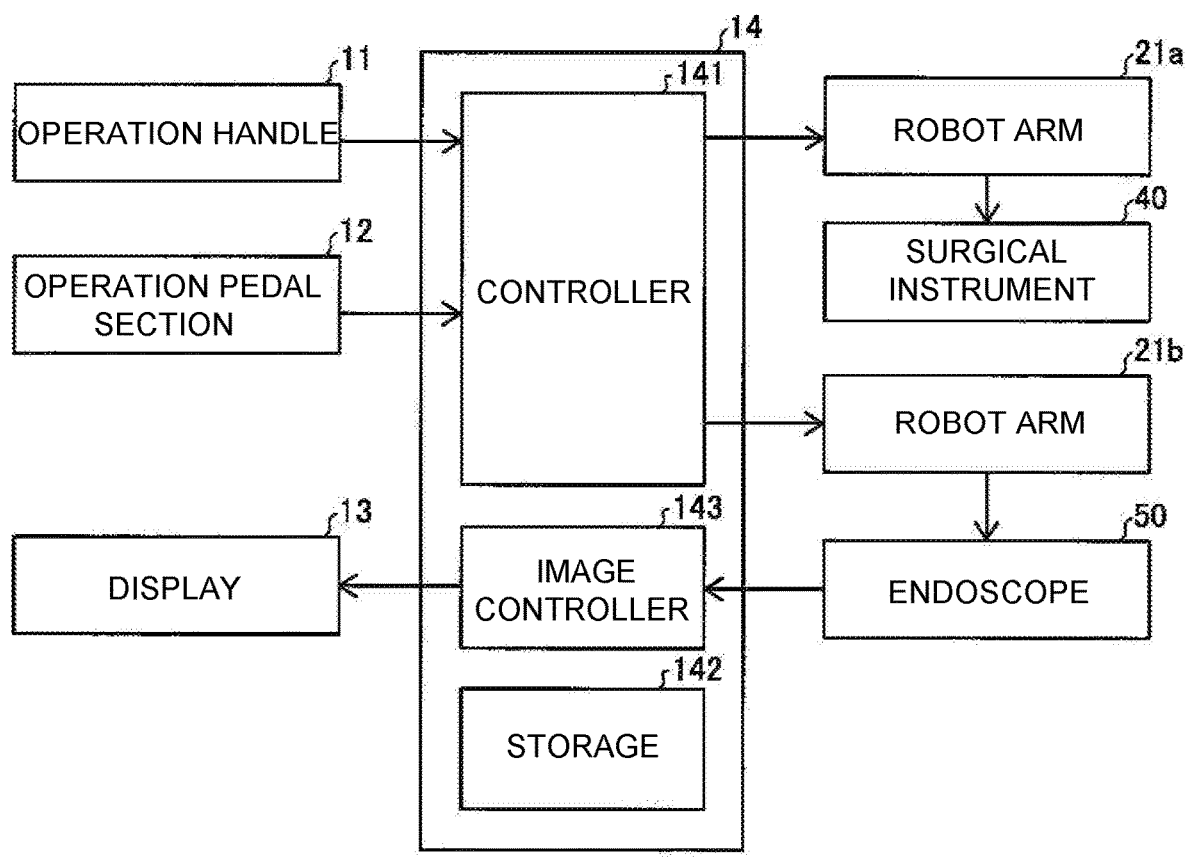
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display 13, and a control apparatus 14.

The operation handles 11 are provided in order to remotely operate the medical equipment attached to the robot arms 21a and 21b. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to 1/2, for example, the end effectors 41 of the surgical instruments 40 move 1/2 of the movement distance of the operation handles 11. This allows for precise fine surgery.

The operation pedal section 12 includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a and 21b to stop movement of the surgical instruments 40. Specifically, when the clutch pedal is being pressed, the robot arms 21a and 21b of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a and 21b. The operator O restarts the operation for the operation handles 11 around the center thereof.

The display 13 is configured to display images captured by the endoscope 50. The display 13 includes a scope type display or a non-scope type display. The scope type display is a display that the operator O looks into. The non-scope type display is a display like an open-type display that includes a flat screen and the operator O is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM (Read Only Memory) and a RAM (Random Access Memory). The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and alternations for the images when needed.

(Configuration of Surgical Instrument, Adaptor, Drape, and Robot Arm)

With reference to FIGS. 3 to 11, the configurations of the surgical instrument 40, adaptor 60, drape 70, and robot arm 21a are described below.

Figure 3:
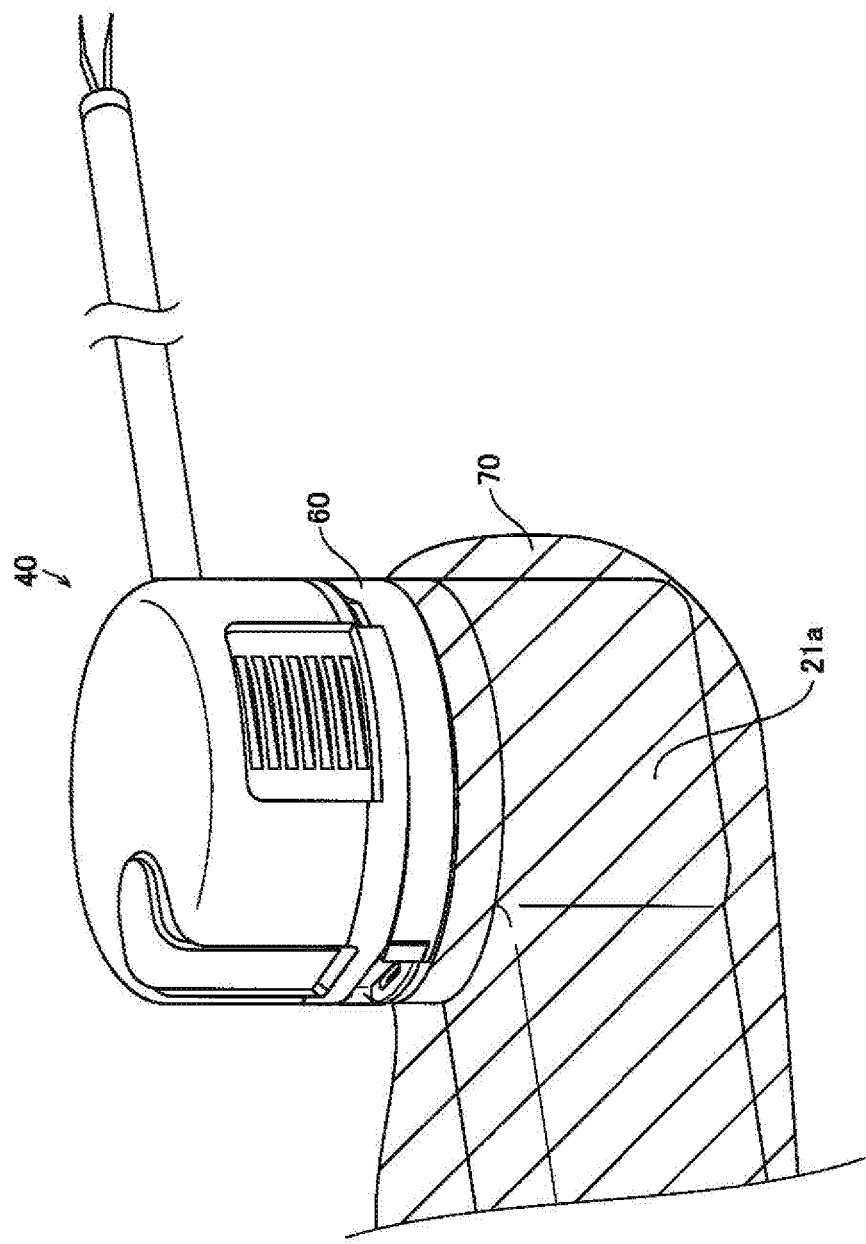
FIG. 3 is a diagram illustrating a perspective view of a state where a surgical instrument is attached to a drive part of the robot arm through an adaptor according to an embodiment.
Figure 4:
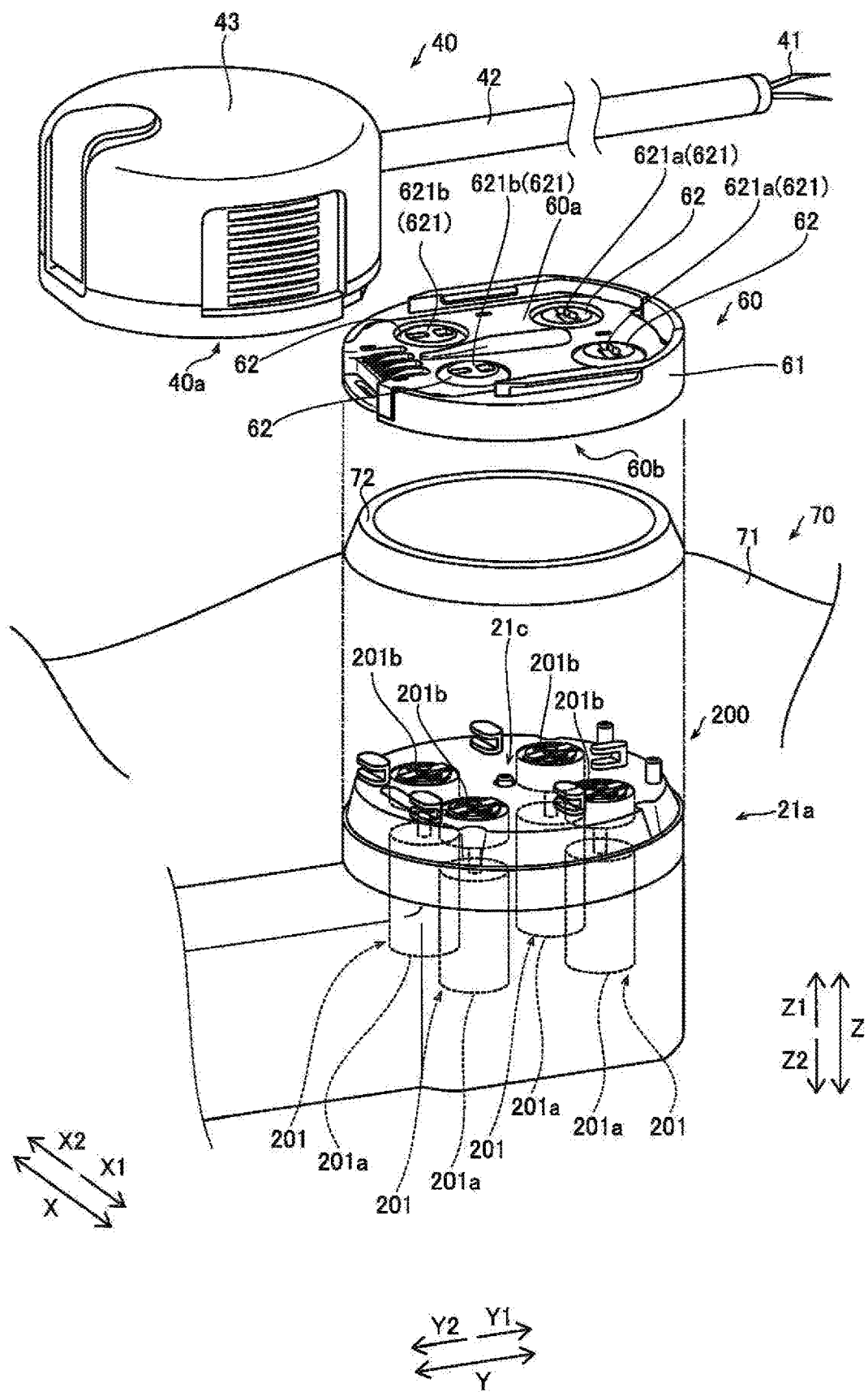
FIG. 4 is a diagram illustrating a perspective view of a state where the surgical instrument and the adaptor are detached from the drive part of the robot arm according to an embodiment.
Figure 5:
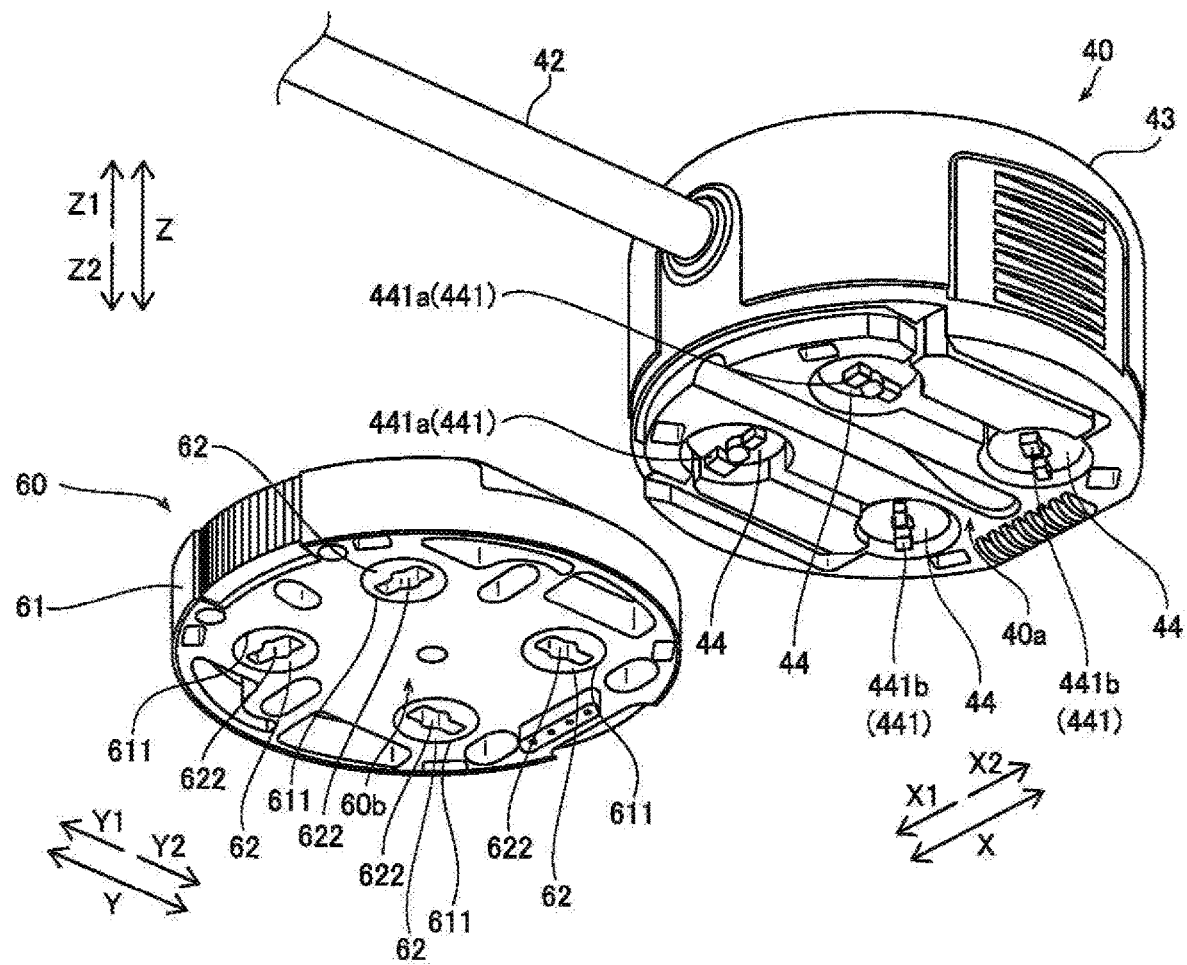
FIG. 5 is a diagram illustrating a perspective view of the adaptor and surgical instrument as seen in Z2 direction according to an embodiment.
Figure 7:
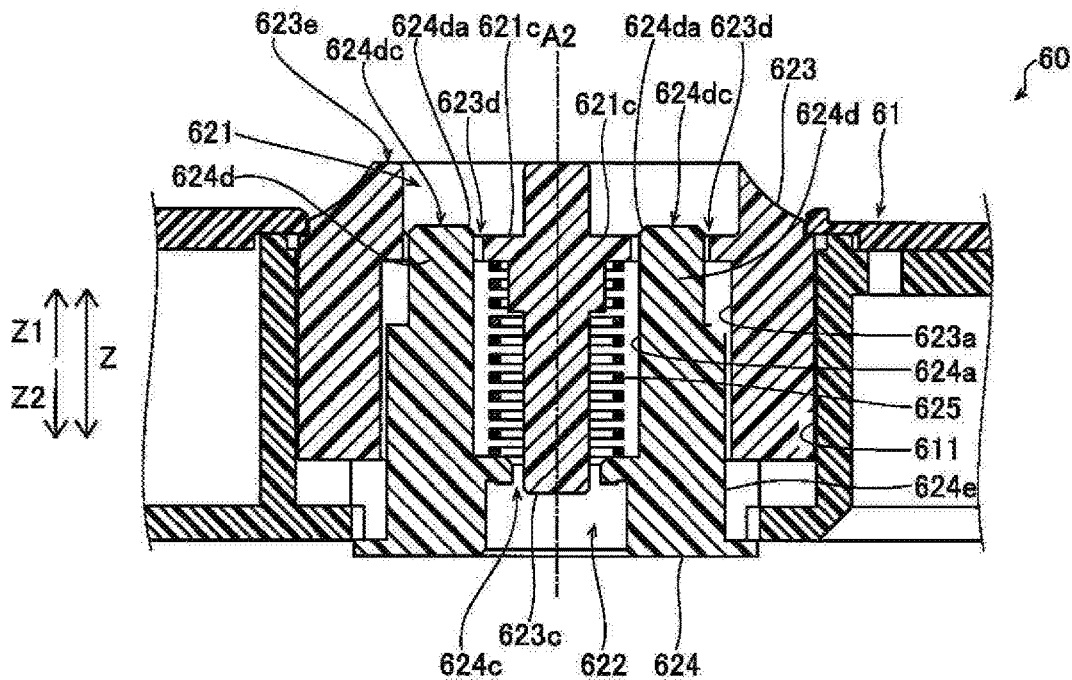
FIG. 7 is a diagram illustrating a schematic cross sectional view of a state where the drive transmission member is held by an adaptor main body of the adaptor according to an embodiment.

As illustrated in FIGS. 3 to 5, the surgical instrument 40 is detachably connected to the robot arm 21a through the adaptor 60. The adaptor 60 is provided between a drive part 200 (described later) of the robot arm 21a and the surgical instrument 40. The adaptor 60 is a drape adaptor to hold a drape 70, and is to be replaced by the user every time the surgery is performed. Thus, the drape 70 can be held by using the adaptor 60. The drape 70 is a sterile drape for covering the robot arm 21a and has been sterilized. The adaptor 60 is configured to sandwich the drape 70 between the adaptor 60 and the robot arm 21a. Note that the adaptor 60 and the drape 70 may be integrally formed with each other.

An attachment surface 40a of a housing 43 of the surgical instrument 40, provided on the Z2 side of the surgical instrument 40, is attached to the adaptor 60. An attachment surface 60a of the adaptor 60, provided on the Z1 side of the adaptor 60, is attached to the surgical instrument 40. An attachment surface 60b of the adaptor 60, provided on the Z2 side of the adaptor 60, is attached to the drive part 200 of the robot arm 21a. An attachment surface 21c of the drive part 200 of the robot arm 21a, provided on the Z1 side of the drive part 200, is attached to the adaptor 60.

The robot arm 21a is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 includes a main body portion 71 and an attachment portion 72. The main body portion 71 covers the robot arm 21a. The attachment portion 72 is sandwiched between the drive part 200 of the robot arm 21a and adaptor 60. The main body portion 71 is made of a flexible film member. The flexible film member is made of a resin material, such as thermoplastic polyurethane, polyethylene, or the like. The main body portion 71 includes an opening so that the drive part 200 of the robot arm 21a is engaged with the adaptor 60. In the opening of the main body portion 71, the attachment portion 72 is provided so as to close the opening. The attachment portion 72 is made of a resin mold member. The resin mold member is made of a resin member such as polyethylene terephthalate or the like. The attachment portion 72 is harder (less flexible) than the main body portion 71. The attachment portion 72 includes an opening so that the drive part 200 of the robot arm 21a is engaged with the adaptor 60. The opening of the attachment portion 72 may be provided corresponding to a portion where the drive part 200 of the robot arm 21a is engaged with the adaptor 60. The opening of the attachment portion 72 may include plural openings corresponding to plural portions at which the drive part 200 of the robot arm 21a is engaged with the adaptor 60.

The surgical instrument 40 includes plural (four) driven members 44 (see FIG. 5), which are provided within the housing 43 and are rotatable about respective rotation axes A1 (see FIG. 10) extending along the Z axis. The plural driven members 44 are provided to operate (drive) the end effector 41. For example, the driven members 44 are connected to the end effector 41 with elongated elements (not illustrated) such as wires and/or cables inserted through the shaft 42. The driven members 44 are rotated to drive the wires, which operate (drive) the end effector 41. In addition, the driven members 44 are connected to the shaft 42 through gears (not illustrated), for example. The shaft 42 is thereby rotated with rotation of the driven members 44, and the end effector 41 is rotated with the rotation of the shaft 42.

Each of the driven members 44 is formed with a fitting projection 441 to be fitted to the corresponding one of drive transmission members 62 (described later) of the adaptor 60, to transmit the driving force from the drive part 200 of the robot arm 21a. The fitting projection 441 is projected from a surface of the driven member 44, provided on the Z2 side of the driven member 44, toward the adaptor 60 in the Z2 direction. The fitting projections 441 of the driven members 44 includes fitting projections 441a of the driven members provided on the Y1 side and fitting projections 441b of the driven members 44 provided on the Y2 side, wherein the fitting projection 441a and the fitting projection 441b are different from each other in shape. The fitting projection 441a and the fitting projection 441b are formed in shapes corresponding to shapes of later described fitting recesses 621a and fitting recesses 621b of the adaptor 60, respectively.

The adaptor 60 includes an adaptor main body 61 and plural (four) drive transmission members 62 held in the adaptor main body 61 to be rotatable about respective rotational axis A2 (see FIG. 6A) extending in the Z direction. The adaptor main body 61 includes plural (four) through holes 611 extending in the Z direction through the adaptor main body 61. In each of the through holes 611, the drive transmission member 62 is provided to be rotatable about the rotational axis A2. The plural (four) drive transmission members 62 are provided corresponding to the plural (four) driven members 44 of the surgical instrument 40. The drive transmission members 62 are configured to transmit the driving force from the robot arm 21a to the driven members 44 of the surgical instrument 40. Each of the drive transmission members 62 includes a fitting recess 621 (see FIG. 4) to be fitted to a fitting projection 441 of the corresponding one of the driven members 44 of the surgical instrument 40. The fitting recess 621 is formed to be recessed from a surface of the drive transmission member 62 provided on the side of the surgical instrument 40 (the Z1 side surface of the drive transmission member 62) in the direction (Z2 direction) away from the surgical instrument 40. The fitting recesses 621 of the drive transmission members 62 include fitting recesses 621a of the drive transmission members 62 provided on the Y1 side and fitting recesses 621b of the drive transmission members 62 provided on the Y2 side, wherein the fitting recess 621a and the fitting recesses 621b are different from each other in shape.

Each of the drive transmission members 62 also includes a fitting recess 622 (see FIG. 5) to be fitted to a fitting projection 201b of the corresponding one of driving members 201 (described later) of the drive part 200 of the robot arm 21a. The fitting recess 622 is formed to be recessed from the surface of the drive transmission member 62 on the robot arm 21a side (the Z2 side surface of the drive transmission member 62) in the direction (Z1 direction) away from the robot arm 21a. Note that the drive transmission members 62 have substantially the same configuration except that the fitting recess 621a and the fitting recess 621b are different from each other in shape.

The robot arm 21a includes the drive part 200 for driving the driven members 44 of the surgical instrument 40. The drive part 200 generates the driving force to be applied to the driven members 44 of the surgical instrument 40. Specifically, the drive part 200 includes plural (four) driving members 201 provided corresponding to the plural (four) driven members 44 of the surgical instrument 40. Each of the driving members 201 includes an actuator 201a including a motor serving as a driving source and the fitting projection 201b configured to be rotated by the actuator 201a about a rotational axis A3 (see FIG. 8) extending along the Z direction. The fitting projection 201b is projected from the Z1 side surface of the driving member 201 toward the adaptor 60 (the Z1 side).

(Configuration of Drive Transmission Member of Adaptor)

As illustrated in FIGS. 6A, 6B, and 7 to 11, each of the drive transmission members 62 includes a first member 623 including the fitting recesses 621, to be fitted to the driven member 44 of the surgical instrument 40, and a second member 624 including the fitting recess 622, to be fitted to the driving member 201 of the drive part 200 of the robot arm 21a. The first member 623 is provided on the side of the attachment surface 60a (the Z1 side), and the second member 624 is provided on the side of the attachment surface 60b (the Z2 side). The first member 623 includes a fitting recess 623a to be fitted to the second member 624. The second member 624 includes an accommodation recess 624a in which a spring 625 is accommodated. The first member 623 and the second member 624 are fitted to each other with the spring 625 sandwiched therebetween such that the first member 623 and the second member 624 are relatively movable in the Z direction to each other. The first member 623 and the second member 624 are retained by the adaptor main body 61 of the adaptor 60 such that the first member 623 and the second member 624 are movable in the Z direction with respect to the adaptor main body 61. Note that FIGS. 6A and 6B illustrate the drive transmission member 62 that is formed with the fitting recesses 621b and does not illustrate the drive transmission member 62 that is formed with the fitting recesses 621a. However, the drive transmission member 62 that is formed with the fitting recesses 621a has the same configuration as the drive transmission member 62 that is formed with the fitting recesses 621b. The spring 625 is an example of a biasing member.

The first member 623 is relatively movable in the Z direction with respect to the second member 624 with the spring 625 therebetween. That is, the first member 623 is relatively movable with respect to the second member 624 with the spring 625 therebetween toward the surgical instrument 40 (the Z1 side) and toward the drive part 200 (the Z2 side). With this, the first member 623 can be easily moved with respect to the second member 624 by using the spring 625. Upon mounting the surgical instrument 40 to the adaptor 60, the first member 623 of the drive transmission member 62 can be moved so as to be depressed in the Z2 direction. The second member 624 is relatively movable in the Z direction with respect to the first member 623 with the spring 625 therebetween. That is, the second member 624 is relatively movable with respect to the first member 623 with the spring 625 therebetween toward the surgical instrument 40 (the Z1 side) and toward the drive part 200 (the Z2 side). With this, the second member 624 can be easily moved with respect to the first member 623 by using the spring 625.

Upon mounting the adaptor 60 to the drive part 200 of the robot arm 21a, the second member 624 of the drive transmission member 62 can be moved so as to be depressed in the Z1 direction. The spring 625 biases the first member 623 in the Z1 direction and biases the second member 624 in the Z2 direction. The spring 625 may be a compression spring (a compression coil spring).

The first member 623 and the second member 624 are rotated integrally with each other about the rotational axis A2 extending the Z direction. Specifically, the first member 623 includes fitting projections 623b fitted to the second member 624, so as to be engaged with the second member 624 with respect to the rotation direction. The second member 624 includes fitting recesses 624b fitted to the first member 623 so as to be engaged with the first member 623 with respect to the rotation direction. The fitting projections 623b are projected inwardly from an inner circumferential surface of the fitting recess 623a of the first member 623, and are engaged with the fitting recesses 624b of the second member 624. The fitting recesses 624b are recessed inwardly from an outer circumferential surface of the second member 624, and are engaged with the fitting projections 623b of the first member 623. The engagement between the fitting recesses 624b of the second member 624 and the fitting projections 623b of the first member 623 is maintained even when one of the first member 623 and the second member 624 is relatively moved in the Z direction with respect to the other with the spring 625 therebetween. With this, even when one of the first member 623 and the second member 624 is moved in the Z direction relative to the other with the spring 625 therebetween, the first member 623 and the second member 624 of the drive transmission members 62 can be rotated integrally with each other.

The second member 624 includes through hole 624c provided at the fitting recess 622. The through hole 624c penetrates through the second member 624 in the direction of the rotational axis A2 (the Z direction). The through hole 624c has substantially a circular shape as viewed in the direction of the rotational axis A2. The first member 623 includes an insertion part 623c inserted in the through hole 624c of the second member 624 in the Z direction. The insertion part 623c extends in the direction of the rotational axis A2. The insertion part 623c has substantially a circular column shape. The through hole 624c of the second member 624 and the insertion part 623c of the first member 623 are disposed to be aligned with the rotation center of the drive transmission member 62. The spring 625 is provided to surround the insertion part 623c.

The second member 624 includes projections 624d, serving as a movement restriction part or a stopper, to restrict (stop) the second member 624 from moving toward the surgical instrument 40 (the Z1 side). Specifically, in the state where the driving member 201 of the drive part 200 is fitted to the second member 624 and the driven members 44 of the surgical instrument 40 is fitted to the first member 623, the projections 624d of the second member 624 come in contact with the driven members 44 of the surgical instrument 40, so as to prevent the second member 624 from moving toward the surgical instrument 40 (the Z1 side). With this, when the second member 624 of the drive transmission member 62 of the adaptor 60 tries to move to the surgical instrument 40 due to an external force such as large vibration, the projections 624d and the driven member 44 of the surgical instrument 40 come in contact with each other so as to restrict the movement of the second member 624 of the drive transmission member 62 of the adaptor 60 toward the surgical instrument 40. Accordingly, the fitting state between the second member 624 of the drive transmission member 62 of the adaptor 60 and the driving member 201 of the drive part 200 can be securely maintained.

Each of the projections 624d includes a distal end portion 624da which is an end portion of the projection 624d on the side of the surgical instrument 40 (the Z1 side) and a proximal end portion 624db (base portion) which is an end portion of the projection 624d on the side of the drive part 200 (the Z2 side). The projection 624d extends in the direction of the rotational axis (the Z direction) from the proximal end portion 624db side (the Z2 side) to the distal end portion 624da side (the Z1 side). The projection 624d has substantially a circular column shape.

The distal end portion 624da of the projection 624d includes a flat surface 624dc opposed to the driven member 44 of the surgical instrument 40 in the Z direction. The surface 624dc is a contact surface that is brough into contact with the driven member 44 of the surgical instrument 40 upon preventing the second member 624 from moving toward the surgical instrument 40 (the Z1 side). More specifically, the surface 624dc of the distal end portion of the projection 624d is to be brought in contact with a surface 441c of the fitting projection 441 of the driven member 44 of the surgical instrument 40. The surface 441c is a flat surface opposed to the surface 624dc in the Z direction. The proximal end portion 624db of each of the projections 624d is integrally formed with a circumferential wall 624e of the second member 624, so that the elongated projections 624d are firmly supported at the proximal end portions 624db thereof. The circumferential wall 624e is a portion to be fitted in the fitting recess 623a of the first member 623. The circumferential wall 624e extends in the rotational direction of the drive transmission member 62.

In an embodiment, in the state where the driving member 201 of the drive part 200 is fitted to the second member 624 and the driven member 44 of the surgical instrument 40 is fitted to the first member 623, there are gaps 626 (see FIG. 11) between the projections 624d of the drive transmission member 62 and the driven member 44 of the surgical instrument 40. When the second member 624 is moved toward the surgical instrument 40 (the Z1 side) by the length of the gap 626, the projections 624d is brought in contact with the driven member 44 of the surgical instrument 40 so as to restrict the second member 624 from moving toward the surgical instrument 40. This securely maintains the fitting state between the second member 624 and the driving members 201 while securing the freedom of movements of the second member 624 by the length of the gap 626. That is, the fitting state between the second member 624 and the driving member 201 are surely maintained while suppressing the load on the second member 624 by the amount of the freedom of the movements of the second member 624.

The gap 626 is a space between the contact surface (surface 624dc) of the projection 624d to the driven member 44 and the contact surface (surface 441c) of the driven member 44 to the projection 624d. The gap 626 has the length of L1 (see FIG. 11) in a state where the second member 624 has not yet moved toward the surgical instrument 40. The length L1 (along the Z direction) of the gap 626 is larger than zero. The length L1 of the gap 626 is smaller than a fitting height L2 between the second member 624 and the driving member 201 of the drive part 200 (that is, a length along the Z direction of a portion where the second member 624 and the driving member 201 of the drive part 200 are fitted with each other) (see FIG. 11). With this configuration, even when the second member 624 is moved toward the surgical instrument 40, the second member 624 moves toward the surgical instrument 40 only by the length L1 of the gap 626 smaller than the fitting height L2 at the maximum. Thus, the fitting state between the second member 624 and the driving member 201 is securely maintained. Note that the smaller the length L1 of the gap 626 than the fitting height L2 is, the better the fitting state between the second member 624 and the driving member 201 is maintained. The length L1 of the gap 626 may be a half of the fitting height L2, for example.

The length L1 of the gap 626 becomes smaller as the second member 624 moves toward the surgical instrument 40. The length L1 of the gap 626 becomes zero when the projection 624d and the driven member 44 is in contact with each other. The projection 624d can be moved between a state where the projection 624d is not contact with the driven member 44 by the length L1 of the gap 626 and a state where the projection is in contact with the driven member 44 with no gap. Note that the length L1 of the gap 626 is a distance along the Z direction between the contact surface (surface 624dc) of the projection 624d to the driven member 44 and the contact surface (surface 441c) of the driven member 44 to the projection 624d, for example. The fitting height L2 is a fitting amount (overlapping amount) along the Z direction between the second member 624 and the driving member 201 of the drive part 200, for example.

In an embodiment, the first member 623 includes through holes 623d in which the projections 624d of the second member 624 are inserted. Each of the through holes 623d penetrates through the first member 623 in the direction of the rotational axis (the Z direction). Each of the through holes 623d has substantially a circular shape corresponding to the projections 624d, as viewed in the direction of the rotational axis. The through holes 623d are formed at bottom portions 621c of the fitting recesses 621 of the first member 623. The projections 624d extend through the through holes 623d of the fitting recesses 621 and are exposed to the first member 623 side (the Z1 side). In the state where the driving member 201 of the drive part 200 is fitted to the second member 624 and the driven member 44 of the surgical instrument 40 is fitted to the first member 623, when the second member 624 is moved toward the surgical instrument 40, the projections 624d are brough in contact with the fitting projections 441 of the driven member 44 within the fitting recesses 621 of the first member 623. Accordingly, by using the fitting projections 441 of the driven member 44, the second member 624 can be restricted from moving toward the surgical instrument 40. Thus, it is not necessary to provide a dedicated movement restriction part at the driven member 44. Therefore, it is possible to restrict the movement of the second member 624 toward the surgical instrument 40 while suppressing the structures of the driven members 44 from becoming complicated.

The projection 624d is provided such that the distal end portion 624da of the projection 624d is located in the vicinity of the bottom portion 621c of the fitting recess 621 of the first member 623 in the state where the driving member 201 of the drive part 200 is fitted to the second member 624. That is, the projection 624d is provided such that the distal end portion 624da of the projection 624d is located in the vicinity of the bottom portion 621c of the fitting recess 621 of the first member 623 in the state where the second member 624 has been maximumly moved toward the drive part 200 (the X2 side). This configuration can minimize projected amounts of the projections 624d within the fitting recesses 621 of the first member 623. Therefore, the fitting amount (overlapping amount) between the fitting projection 441 of the driven member 44 and the fitting recess 621 of the first member 623 can be easily secured.

The projection 624d is provided not to be projected such that the distal end portion 624da of the projection 624d is not projected from the end surface 623e of the first member 623 on the surgical instrument 40 side toward the surgical instrument 40. This can prevent an external force from being unintentionally applied to the distal end portion 624da of the projection 624d, and thus prevent a load from being applied to the projection 624d, unlike a case where the distal end portion 624da of the projection 624d is projected from the end surface 623e of the first member 623. In the state where the second member 624 has been maximumly moved toward the surgical instrument 40 (the Z1 side), the projection 624d is provided such that the distal end portion 624da of the projection 624d is located in the vicinity of the end surface 623e of the first member 623.

In an embodiment, the plural (two) projections 624d are provided to correspond to the plural (two) fitting projections 441 of the driven members 44. With this, upon restricting the movement of the second member 624 toward the surgical instrument 40, the plural fitting projections 441 come in contact with the plural projections 624d. Therefore, it is possible to securely restrict the movement of the second member 624 toward the surgical instrument 4. The plural projections 624d are provided at equal intervals about the rotational axis of the drive transmission member 62. With this, unlike a case where the plural projections 624d are unevenly (unbalancedly) located about the rotational axis of the drive transmission members 62, it is possible, upon restricting the movement of the second member 624 toward the surgical instrument 40, to prevent a portion where the projections 624d do not restrict the movement of the second member 624 from being inclined with respect to a portion where the projections 624d restricts the movement of the second member 624. Therefore, it is possible to prevent the second member 624 from being inclined upon the restriction of the movement of the second member 624 toward the surgical instrument 40. The plural projections 624d are provided at the equal distances from the rotational axis of the drive transmission member 62 and provided equiangularly (at 180 degrees in an embodiment) along the rotational direction of the drive transmission member 62.

(Attachment of Adaptor and Surgical Instrument)

Next, with reference to FIGS. 8 to 11, an attachment of the adaptor 60 to the drive part 200 of the robot arm 21a, and an attachment of the surgical instrument 40 to the adaptor 60 are described. In the patient-side apparatus 20, after the adaptor 60 is attached to the drive part 200 of the robot arm 21a, the surgical instrument 40 is attached to the adaptor 60 that has been attached to the drive part 200. Note that in FIGS. 8 to 11, the fitting projection 201b of the driving member 201 of the drive part 200 is simplified to facilitate understanding. Similarly, in FIGS. 10 and 11, the fitting projections 441 of the driven member 44 of the surgical instrument 40 are simplified to facilitate understanding.

Figure 8:
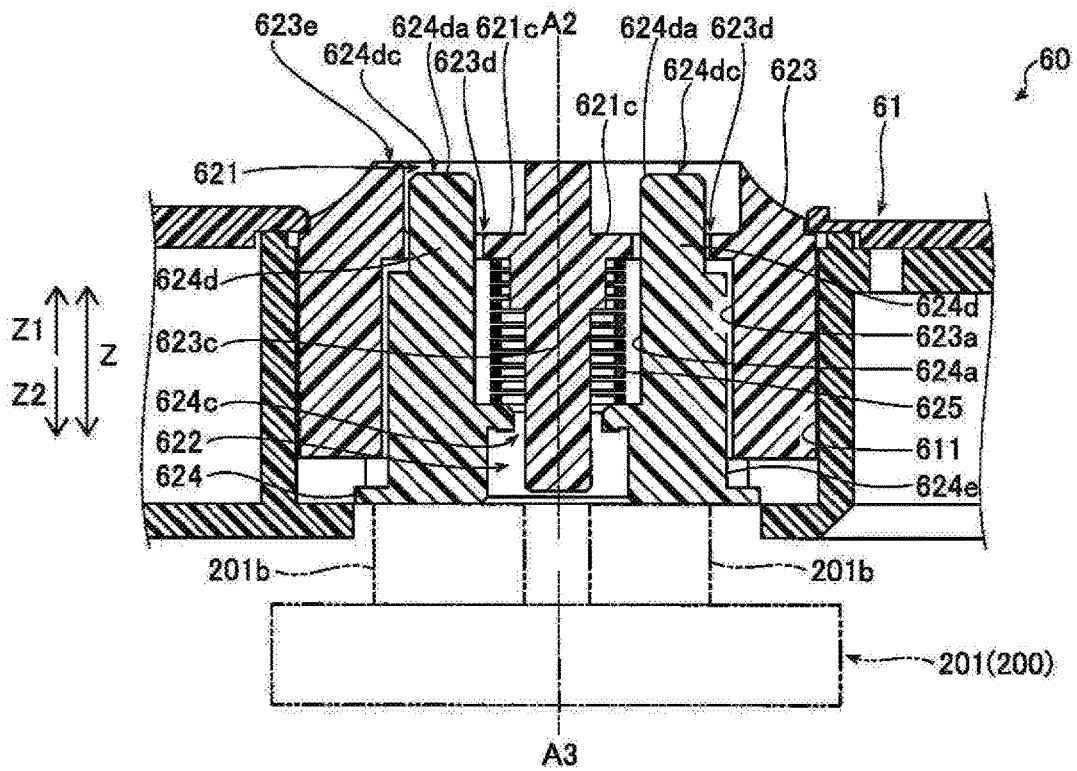
FIG. 8 is a diagram illustrating a schematic view of a state where the adaptor is mounted on but is not fitted to the drive part of the robot arm according to an embodiment.
Figure 9:
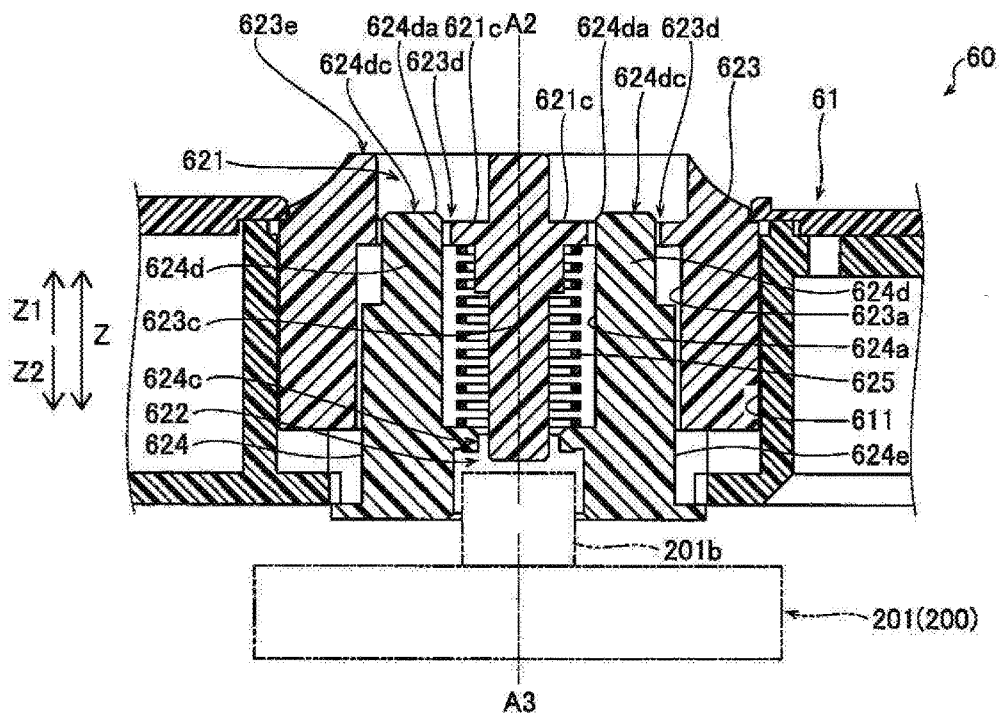
FIG. 9 is a diagram illustrating a schematic cross-sectional view of a state where the adaptor is mounted on and fitted to the drive part of the robot arm according to an embodiment.

First, with reference to FIGS. 8 and 9, an attachment of the adaptor 60 to the drive part 200 of the robot arm 21a is described. Note that even through the drape 70 is omitted for illustration in the Figures, the attachment of the adaptor 60 to the drive part 200 of the robot arm 21a is executed with the drape 70 sandwiched between the drive part 200 and the adaptor 60.

FIG. 8 is a diagram illustrating a view of a state where the adaptor 60 is mounted to the drive part 200 of the robot arm 21a but the driving members 201 of the drive part 200 are not yet fitted to the drive transmission members 62 of the adaptor 60. In this state, the second member 624 is pushed toward the surgical instrument 40 (the Z1 side) by means of the fitting projection 201b of the driving member 201, and thus the second member 624 is moved in the Z1 direction with respect to the first member 623 with the spring 625 sandwiched therebetween. At this time, the projection 624d of the second member 624 is inserted in the through holes 623d of the first member 623 along the direction of the rotational axis (the Z direction) in such a manner that the distal end portion 624da of the projection 624d of the second member 624 is not projected from the end surface 623e of the first member 623.

In the state where the fitting projection 201b of the driving member 201 pushes the second member 624 in the Z1 direction, the driving members 201 is rotated about the rotational axis A3. This moves the fitting projection 201b of the driving member 201 to a position where the fitting projection 201b of the driving member 201 is fitted to the fitting recess 622 of the second member 624. Therefore, as illustrated in FIG. 9, the second member 624 is moved toward the drive part 200 (the Z2 side) with respect to the first member 623 with the spring 625 therebetween and the fitting projection 201b of the driving member 201 and the fitting recess 622 of the second member 624 are fitted to each other. The fitting amount (overlapping amount) between the fitting projection 201b of the driving member 201 and the fitting recess 622 of the second member 624 is the length L2 (see FIG. 11). In this state, the drive transmission members 62 can receive the driving force of the driving members 201, so that the drive transmission members 62 can be rotated about the rotational axis A2 by the driving force of the driving members 201. In this state, the projections 624d of the second member 624 are inserted in the through holes 623d of the first member 623 in the direction of the rotational axis (the Z direction) in such a manner that the distal end portions 624da of the projections 624d are located in the vicinity of the bottom portions 621c of the fitting recesses 621 of the first member 623.

Figure 10:
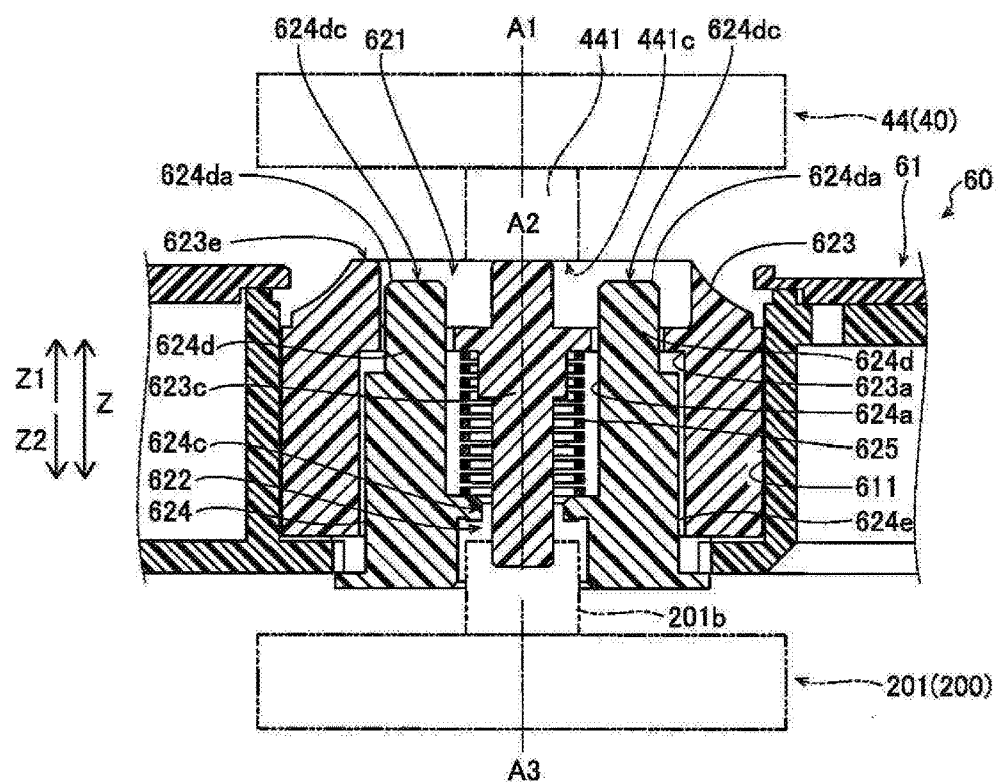
FIG. 10 is a diagram illustrating a schematic cross-sectional view of a state where the surgical instrument is mounted on but is not fitted to the adaptor according to an embodiment.
Figure 11:
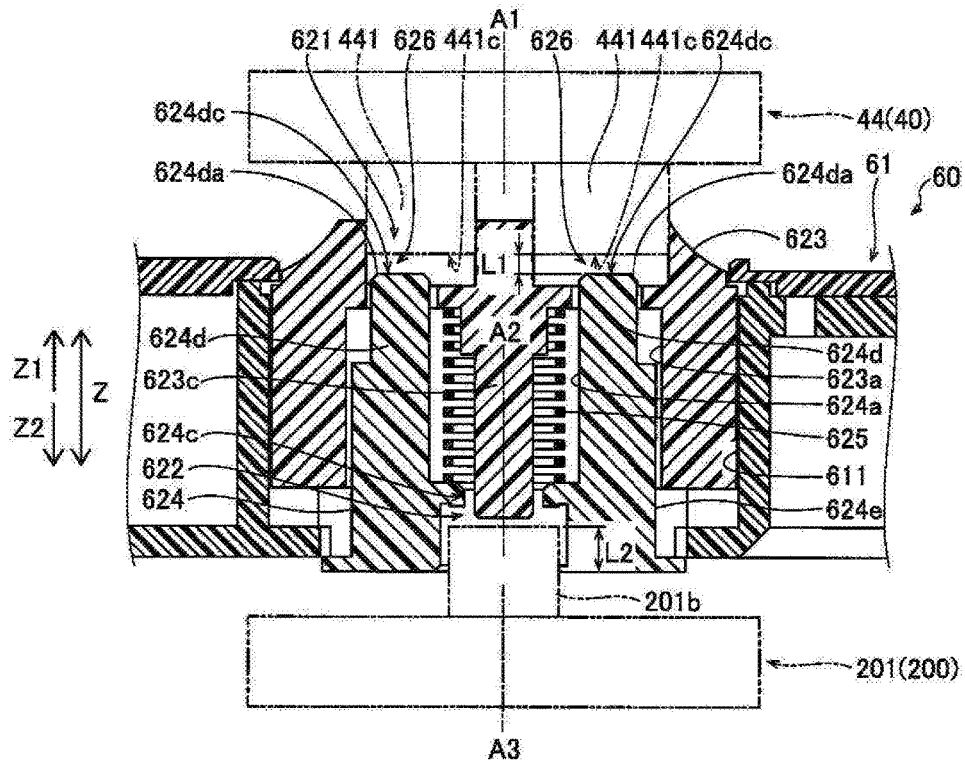
FIG. 11 is a diagram illustrating a schematic cross-sectional view of a state where the surgical instrument is mounted on and is fitted to the adaptor according to an embodiment.

Next, with reference to FIGS. 10 and 11, an attachment of the surgical instrument 40 to the adaptor 60 is described.

FIG. 10 is a diagram illustrating a view of a state where the surgical instrument 40 is mounted to the adaptor 60 that has been attached to the drive part 200 of the robot arm 21a but the drive transmission members 62 of the adaptor 60 are not yet fitted to the driven members 44 of the surgical instrument 40. In this state, the fitting projection 441 of the driven member 44 pushes the first member 623 toward the drive part 200 (the Z2 side), and thus the first member 623 is moved in the Z2 direction with respect to the second member 624 with the spring 625 therebetween. In this state, the projection 624d of the second member 624 is inserted in the through holes 623d of the first member 623 in the direction of the rotational axis (the Z direction) in such a manner that the distal end portion 624da of the projection 624d is not projected from the end surface 623e of the first member 623.

Then, in the state where the first member 623 is pushed in the Z2 direction by the fitting projections 441 of the driven member 44, the drive transmission member 62 is rotated about the rotational axis A2 by the driving member 201. With this, the fitting recesses 621 of the first member 623 of the drive transmission member 62 are moved to a position where the fitting recesses 621 of the first member 623 are fitted to the fitting projections 441 of the driven member 44. As a result, as illustrated in FIG. 11, the first member 623 is moved toward the surgical instrument 40 (the Z1 side) with respect to the second member 624 with the spring 625 therebetween, and thus the fitting recesses 621 of the first member 623 are fitted to the fitting projections 441 of the driven member 44. In this state, the driven members 44 can receive the driving forces from the driving members 201 via the drive transmission members 62 so that the driven members 44 can be rotated about the rotational axes A1 by the driving forces through the drive transmission members 62 from the driving members 201. In this state, the projections 624d of the second member 624 are inserted in the through holes 623d of the first member 623 in the direction of the rotational axis (the Z direction) in such a manner that the distal end portions 624da of the projections 624d are located in the vicinity of the bottom portions 621c of the fitting recesses 621 of the first member 623.

Further the gap 626 of the length L1 is provided between the projection 624d of the second member 624 and the corresponding fitting projection 441 of the driven member 44. In this state, even when the second member 624 is moved toward the surgical instrument 40 due to an external force such as large vibration, the projections 624d of the second member 624 come in contact with the driven member 44 of the surgical instrument 40 to restrict the movement of the second member 624 in the Z1 direction. As a result, the fitting state between the second member 624 and the driving members 201 is securely maintained.

(Effects)

According to one or more embodiments described above, up mounting the surgical instrument 40 to the drive part 200 of the robot arm 21a, the first member 623 and the second member 624 of each of the drive transmission members 62 of the adaptor 60 can be moved in the directions toward the surgical instrument 40 and toward the drive part 200. That is, the adaptor 60 includes the components that can move in the directions toward the surgical instrument 40 and toward the drive part 200 when mounting the surgical instrument to the drive part 200. Accordingly, the components that can move in the directions toward the surgical instrument and the drive part can be replaced when replacing the adaptor 60. Since the adaptor 60 is a part that is to be replaced by the user, the adaptor can be easily replaced by the user. Further, because the adaptor 60 is the part that is to be replaced by the user every time the surgery is performed, a usage of the adaptor 60 in a state where the first member 623 and the second member 624 are worn can be prevented.

By the way, in the robot surgery system disclosed in the above-mentioned Japanese Patent No. 5403864, the fitting between the drive part and the adapter may be unintentionally released if the spring load input is worn. Thus, it is conceivable to provide a sensor for detecting the fitting state between the drive part and the adapter in such a surgery system. To the contrary, according to one or more embodiments described above, since the second member 624 is formed with the projections 624d, the fitting state between the drive part 200 and the adaptor 60 is securely maintained, and thus it is not necessary to additionally provide a sensor for detecting the fitting state between the drive part 200 and the adaptor 60.

(Modifications)

It should be understood that one or more embodiments described above are illustrated by way of example in every respect and not limit the invention. The scope of the invention is indicated by claims, not by explanation of one or more embodiments described above, and includes equivalents to claims and all alterations within the same.

Figure 12:
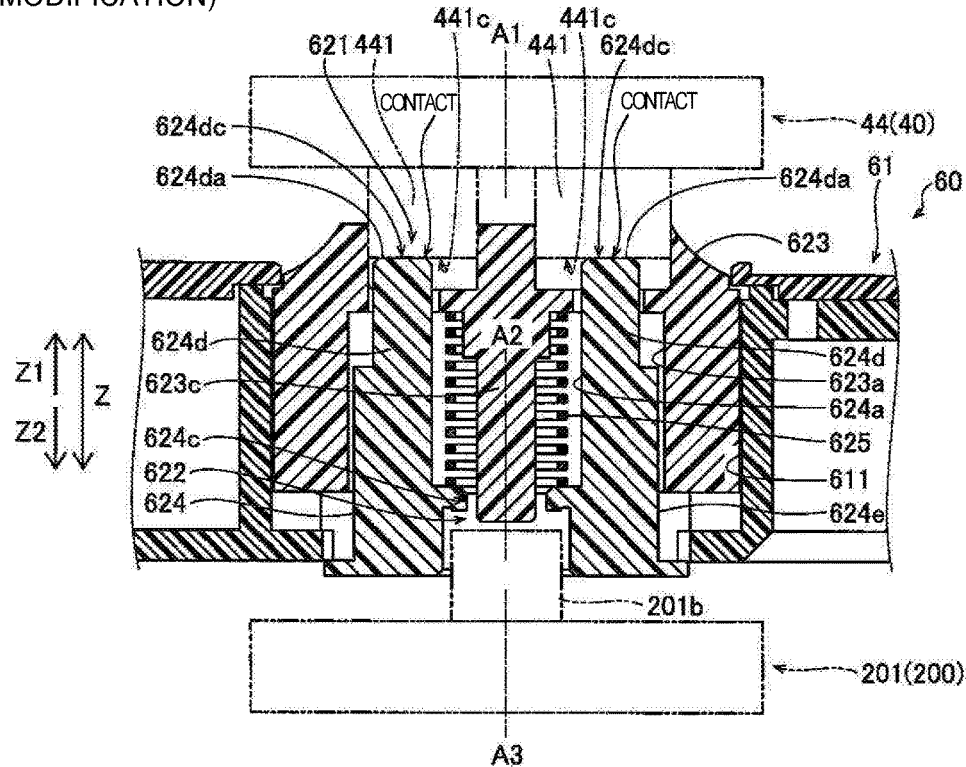
FIG. 12 is a diagram illustrating a schematic cross-sectional view of a state where a surgical instrument is mounted on and is fitted to an adaptor according to a modification.

For example, in one or more embodiments described above, there is the gap between the projection of the second member and the driven member of the surgical instrument. However, the disclosure is not limited to this. In a modification, there may be no gap between the projection of the second member and the driven member of the surgical instrument. For example, in a modification illustrated in FIG. 12, there is no gap between the projection 624d of the second member 624 and the driven member 44 of the surgical instrument 40. That is, in the modification illustrated in FIG. 12, in a state where the driving member 201 of the drive part 200 is fitted to the second member 624 and the driven member 44 of the surgical instrument 40 is fitted to the first member 623, the projections 624d are in contact with the driven member 44 of the surgical instrument 40 (the fitting projections 441), so as to restrict the movement of the second member 624 toward the surgical instrument 40 (the Z1 side). With this, the fitting state between the second member 624 and the driving member 201 is securely maintained.

In one or more embodiments described above, the projections of the second member come in contact with the fitting projections of the driven member of the surgical instrument, to restrict the movement of the second member toward the surgical instrument. However, the disclosure is not limited to this. In a modification, as long as restricting the movement of the second member toward the surgical instrument, the projection(s) of the second member may come in contact with a part or portion other than the fitting projection(s) of the driven member. For example, a projection of the second member may be provided so as to come in contact with a surface of the driven member on the side of the adaptor. In this case, the first member may be formed with a through hole, in which the projection of the second member is inserted, at a portion (for example, the end surface 623e on the side of the surgical instrument) other than the bottom portion of the fitting recess of the first member.

In one or more embodiments described above, the two projections are provided at the second member. However, the disclosure is not limited to this. In a modification, as long as restricting the movement of the second member, the number of the projections of the second member may be one or three or more.

In one or more embodiments described above, the projections of the second member has substantially the circular column shape. However, the disclosure is not limited to this. In a modification, as long as restricting the movement of the second member, the projections of the second member may have a shape different from the circular column shape. For example, the projections of the second member may have a rectangular column shape or may have a shape different from a column shape.

In one or more embodiments described above, the projections of the second member are provided in such a manner that the distal end portions of the projections are located in the vicinity of the bottom portions of the fitting recesses of the first member in the state where the drive part of the driving member is fitted to the second member. However, the disclosure is not limited to this. In a modification, the distal end portions of the projections of the second member may not necessarily be located in the vicinity of the bottom portions of the fitting recesses of the first member in the state where the drive part of the driving member is fitted to the second member.

In one or more embodiments described above, the plural projections of the second member are provided at equal intervals about the rotational axis of the drive transmission member. However, the disclosure is not limited to this. In a modification, one of the plural projections of the second member may be provided at the rotational axis of the drive transmission member and the others of the plural projections of the second member may be provided at equal intervals about the rotational axis of the drive transmission member. Further, in a case where the number of the projections of the second member is one, the one projection may be provided at the rotational axis of the drive transmission member. Furthermore, in a modification, the plural projections of the second member may not be necessarily provided at equal intervals about the rotational axis of the drive transmission member.

In one or more embodiments described above, the projections of the second member are provided in such a manner that the distal end portions of the projections are not projected beyond the end surface of the first member on the side of the surgical instrument. However, the disclosure is not limited to this. In a modification, the projections of the second member may be provided in such a manner that the distal end portions of the projections are projected beyond the end surface of the first member on the side of the surgical instrument.

The invention claimed is:

1. An adaptor to be provided between a drive part provided at a robot arm and including a driving member and a surgical instrument including a driven member, comprising:
a drive transmission member provided to be rotatable to transmit a driving force from the driving member of the drive part to the driven member of the surgical instrument, wherein
the drive transmission member includes:
a first member to be fitted to the driven member of the surgical instrument; and
a second member relatively movable with respect to the first member in directions toward the surgical instrument and toward the drive part, the second member being to be fitted to the driving member of the drive part, wherein
the second member includes a movement restriction part that comes in contact with the driven member of the surgical instrument to thereby restrict a movement of the second member toward the surgical instrument in a state where the driving member of the drive part is fitted to the second member and the driven member of the surgical instrument is fitted to the first member.

2. The adaptor according to claim 1, wherein the movement restriction part includes a projection.

3. The adaptor according to claim 2, wherein a contact surface of the projection to the driven member and a contact surface of the driven member to the projection are both flat surfaces.

4. The adaptor according to claim 2, wherein the projection is provided with a gap between the projection and the driven member of the surgical instrument in the state where the driving member of the drive part is fitted to the second member and the driven member of the surgical instrument is fitted to the first member, such that when the second member is moved toward the surgical instrument, the projection comes in contact with the driven member of the surgical instrument to restrict the movement of the second member toward the surgical instrument.

5. The adaptor according to claim 4, wherein a length of the gap is smaller than a fitting height between the second member and the driving member of the drive part fitted with each other.

6. The adaptor according to claim 5, wherein the length of the gap is not greater than a half of the fitting height.

7. The adaptor according to claim 2, wherein the driven member includes a fitting projection to be fitted to the first member,
the first member includes a fitting recess, wherein the fitting recess is fitted to the fitting projection of the driven member and includes a through hole in which the projection of the second member is inserted, and
the projection of the second member comes in contact with the fitting projection of the driven member within the fitting recess of the first member.

8. The adaptor according to claim 7, wherein the fitting projection of the driven member includes a plurality of fitting projections, and
the projection of the second member includes a plurality of projections, wherein a number of the plurality of fitting projections of the second member corresponds to a number of the plurality of fitting projections of the driven member.

9. The adaptor according to claim 7, wherein the fitting recess of the first member is formed with a bottom portion thereof at which the through hole is formed, and
the projection of the second member includes a distal end portion thereof, such that the distal end portion of the projection is located in a vicinity of the bottom portion of the fitting recess of the first member in the state where the driving member of the drive part is fitted to the second member.

10. The adaptor according to claim 2, wherein the projection of the second member includes a plurality of projections, and
the plurality of projections are provided at equal intervals about a rotational axis of the drive transmission member.

11. The adaptor according to claim 2, wherein the projection of the second member includes a distal end portion thereof, such that the distal end portion of the projection is not projected beyond an end surface of the first member on a side of the surgical instrument.

12. The adaptor according to claim 2, wherein
the second member includes a circumferential wall fitted to the first member, and
the projection of the second member is integrally formed with the circumferential wall of the second member.

13. The adaptor according to claim 12, wherein
the projection of the second member includes a distal end portion at an end portion thereof on a side of the surgical instrument and a proximal end portion at an end portion thereof on a side of the drive part, and
the proximal end portion of the projection of the second member is formed integrally with the circumferential wall of the second member.

14. The adaptor according to claim 1, wherein
the drive transmission member includes a biasing member, and
the second member is relatively movable with respect to the first member in the directions toward the surgical instrument and toward the drive part via the biasing member.

15. The adaptor according to claim 14, wherein
the biasing member is provided between the first member and the second member.

16. The adaptor according to claim 15, wherein
the driving member includes a fitting projection to be fitted to the second member,
the second member includes a fitting recess to be fitted to the fitting projection of the driving member, the fitting recess being formed with a through hole,
the first member includes an insertion part extending in a direction of a rotational axis of the drive transmission member and inserted in the through hole of the second member, and
the biasing member includes a compression coil spring surrounding the insertion part of the first member.

17. The adaptor according to claim 1, wherein
the adaptor is a drape adaptor to hold a drape.

18. The adaptor according to claim 1, wherein
the adaptor is integrally formed with a drape.

19. An adaptor to be provided between a drive part provided at a robot arm and including a driving member and a surgical instrument including a driven member, comprising:
a drive transmission member provided to be rotatable to transmit a driving force from the driving member of the drive part to the driven member of the surgical instrument, wherein
the drive transmission member includes:
a first member to be fitted to the driven member of the surgical instrument; and
a second member relatively movable with respect to the first member in directions toward the surgical instrument and toward the drive part, the second member being to be fitted to the driving member of the drive part, wherein
the second member includes a movement restriction part that is in contact with the driven member of the surgical instrument to restrict a movement of the second member toward the surgical instrument in a state where the driving member of the drive part is fitted to the second member and the driven member of the surgical instrument is fitted to the first member.

20. A robotic surgical system comprising:
a drive part provided at a robot arm and including a driving member;
a surgical instrument including a housing to be attached to the drive part and a driven member rotatably provided in the housing; and
an adaptor to be provided between the drive part and the surgical instrument, wherein
the adaptor includes:
a drive transmission member provided to be rotatable to transmit a driving force from the driving member of the drive part to the driven member of the surgical instrument, wherein
the drive transmission member includes:
a first member to be fitted to the driven member of the surgical instrument; and
a second member relatively movable with respect to the first member in directions toward the surgical instrument and toward the drive part, the second member being to be fitted to the driving member of the drive part, wherein
the second member includes a movement restriction part that comes in contact with the driven member of the surgical instrument to restrict a movement of the second member toward the surgical instrument in a state where the driving member of the drive part is fitted to the second member and the driven member of the surgical instrument is fitted to the first member.

* * * * *